(12) United States Patent
Bootwala

(10) Patent No.: US 10,131,039 B2
(45) Date of Patent: *Nov. 20, 2018

(54) SURGICAL DEVICES AND METHODS FOR DRIVING AN IMPLANT AND APPLYING COUNTER TORQUE

(71) Applicant: MEDOS INTERNATIONAL SARL, Le Locle (CH)

(72) Inventor: Zoher Bootwala, Foxboro, MA (US)

(73) Assignee: Medos International Sàrl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/659,794

(22) Filed: Jul. 26, 2017

(65) Prior Publication Data
US 2018/0009092 A1 Jan. 11, 2018

Related U.S. Application Data

(63) Continuation of application No. 14/746,985, filed on Jun. 23, 2015, now Pat. No. 9,744,654.

(51) Int. Cl.
*B25B 23/00* (2006.01)
*A61B 17/70* (2006.01)
*B25B 17/00* (2006.01)

(52) U.S. Cl.
CPC ...... *B25B 23/0085* (2013.01); *A61B 17/7091* (2013.01); *B25B 17/00* (2013.01)

(58) Field of Classification Search
CPC ............ A61B 17/7032; A61B 17/7082; A61B 17/7083; A61B 17/7091; B25B 23/0085; B25B 17/00

(Continued)

(56) References Cited

U.S. PATENT DOCUMENTS 3,512,423 A 5/1970 Schuitemaker
5,064,375 A 11/1991 Jorneus
(Continued)

FOREIGN PATENT DOCUMENTS

GB 2 110 141 A 6/1983

OTHER PUBLICATIONS

U.S. Appl. No. 14/746,985, filed Jun. 23, 2015, Surgical Devices and Methods for Driving an Implant and Applying Counter Torque.

*Primary Examiner* — Pedro Philogene
*Assistant Examiner* — David C Comstock
(74) *Attorney, Agent, or Firm* — Nutter McClennen & Fish LLP

(57) ABSTRACT

Devices, systems, and methods are provided for driving an implant and applying counter torque. For example, a driver can include a handle, a driver shaft, and a counter torque shaft, the counter torque shaft being laterally offset from the driver shaft. A distal end of each shaft can mate with a specific type of implant and/or anatomy. The shafts can be removed and replaced from the device, allowing a user to select shafts having particular lengths and/or mating tips. In use, distal ends of the shafts can be fixed or constrained relative to one another and to an implant such that the counter torque shaft cannot orbit around the driver shaft. Rotating the handle can rotate the driver shaft, driving the implant. This can cause the counter torque shaft to try to orbit around the driver shaft, but the fixed/constrained ends restrict this motion, applying the counter torque.

17 Claims, 14 Drawing Sheets

(58) Field of Classification Search
USPC ........ 606/246, 264, 270, 279, 99, 104, 86 A
See application file for complete search history.

(56) References Cited

U.S. PATENT DOCUMENTS

| | | |
|---|---|---|
| 7,296,500 B1 | 11/2007 | Martinelli |
| 8,679,117 B2 | 3/2014 | Knuchel et al. |
| 8,960,053 B2 | 2/2015 | Yang |
| 9,744,654 B2 * | 8/2017 | Bootwala ............ A61B 17/7091 |
| 2011/0066156 A1 | 3/2011 | McGahan et al. |
| 2016/0374735 A1 | 12/2016 | Bootwala |

* cited by examiner

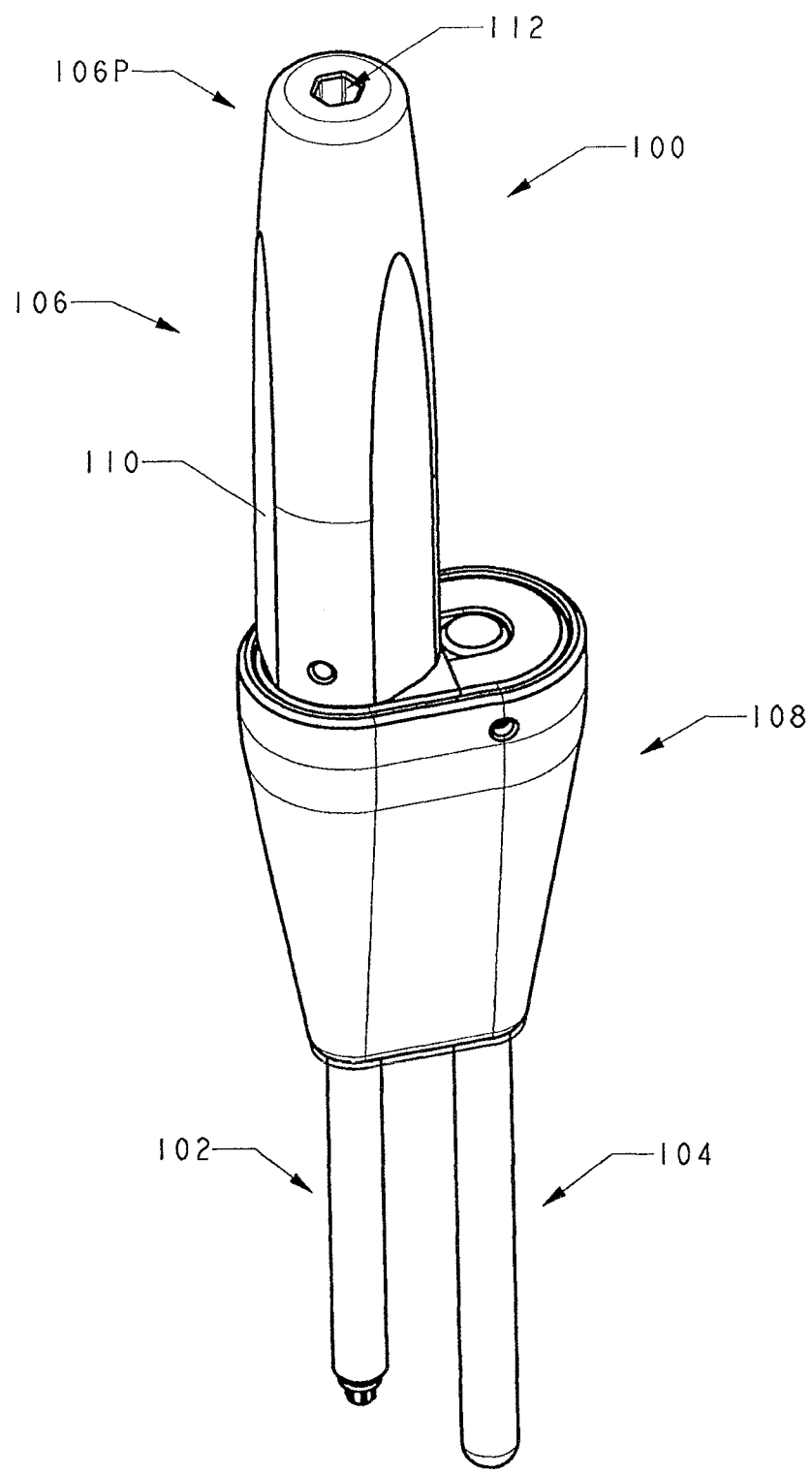

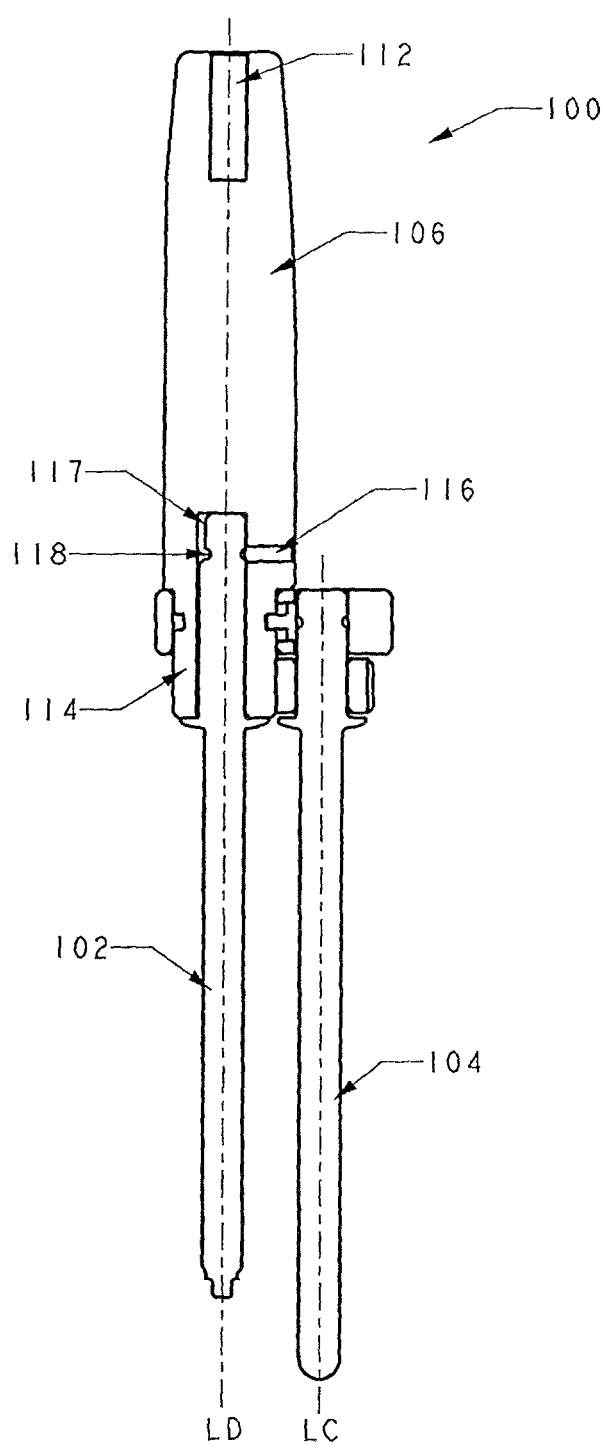

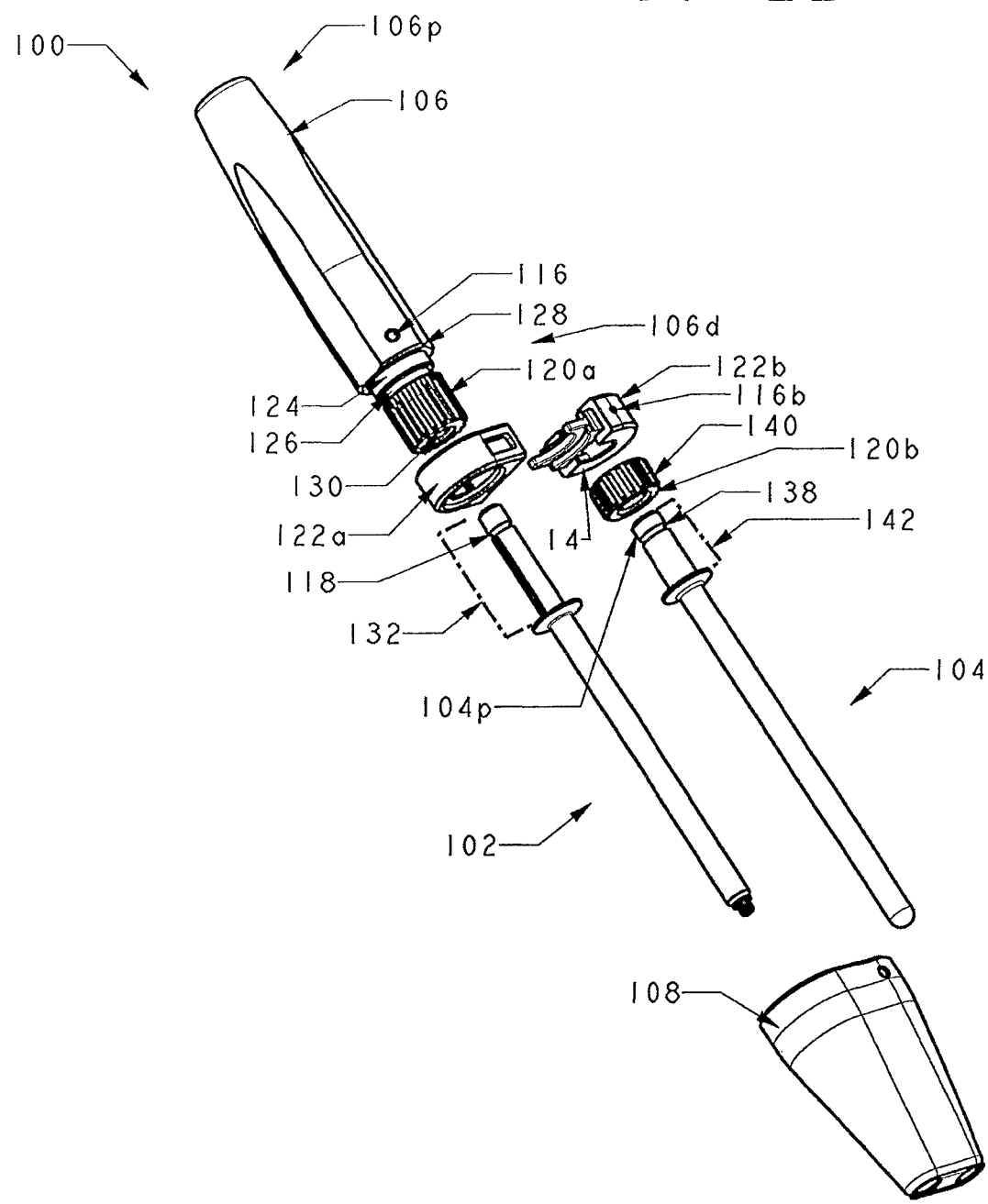

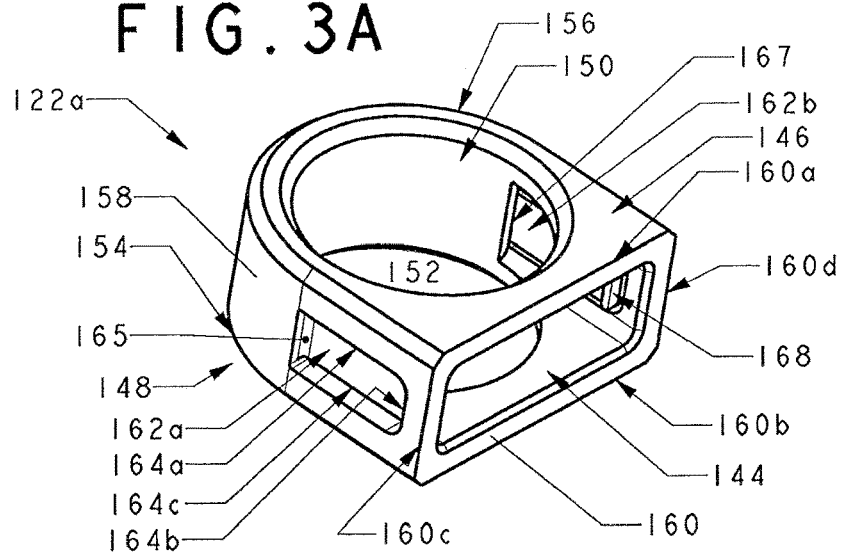
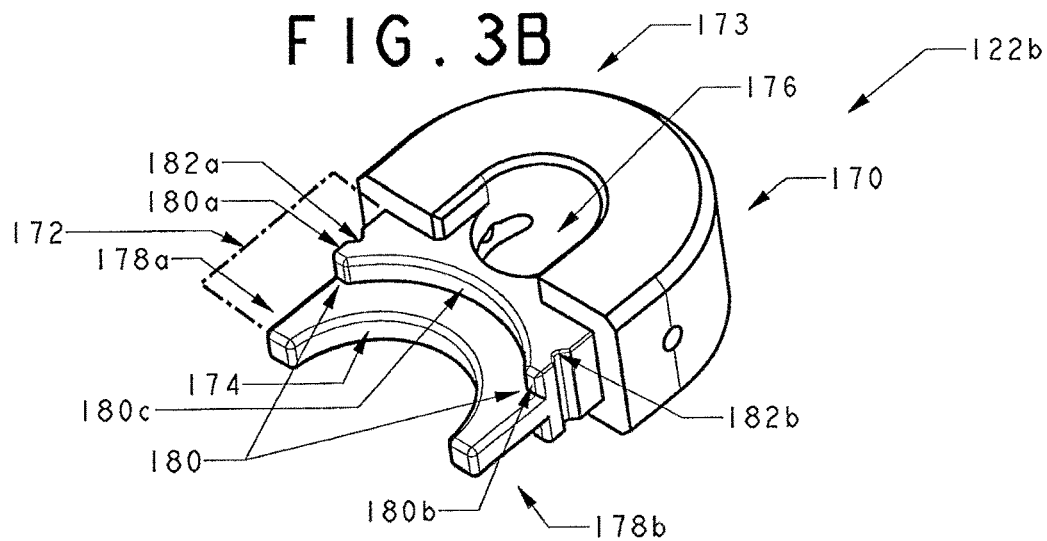
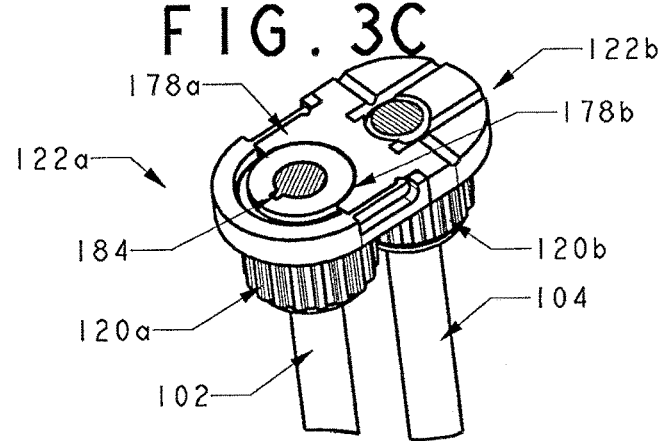

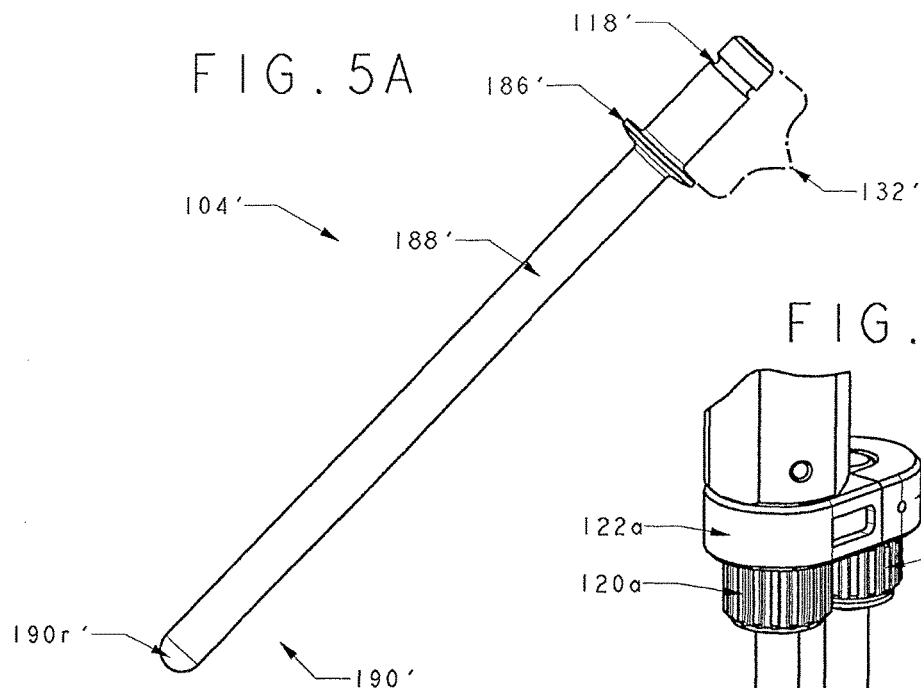
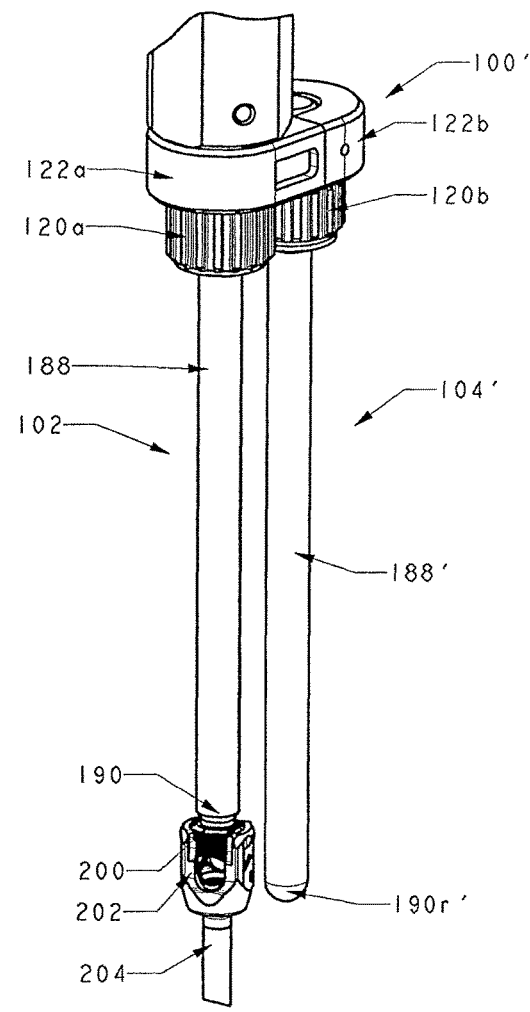

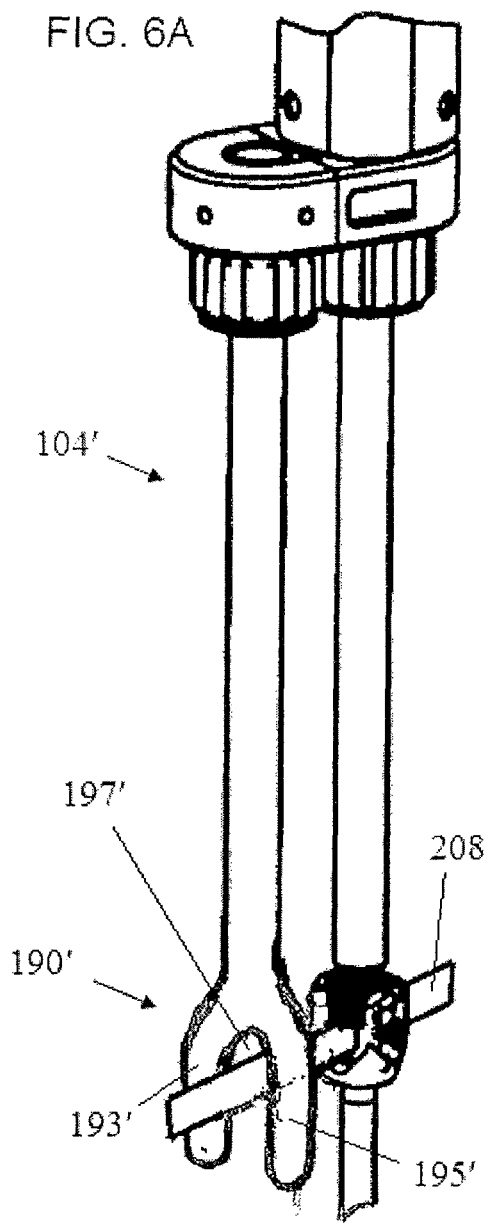

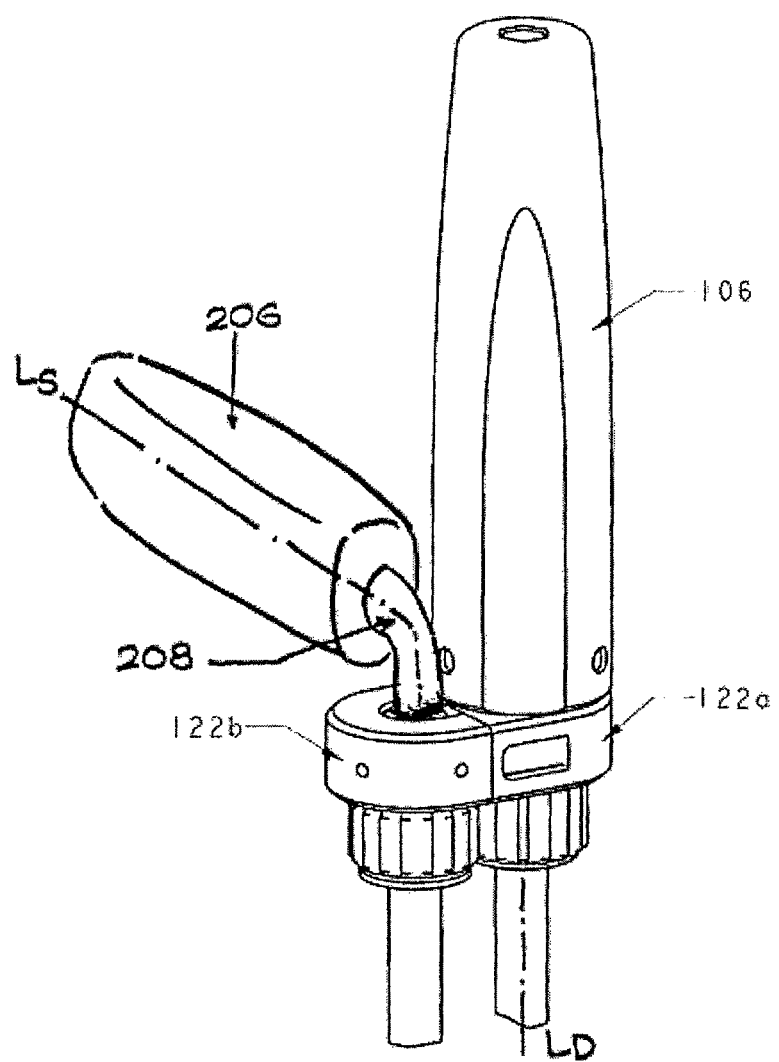

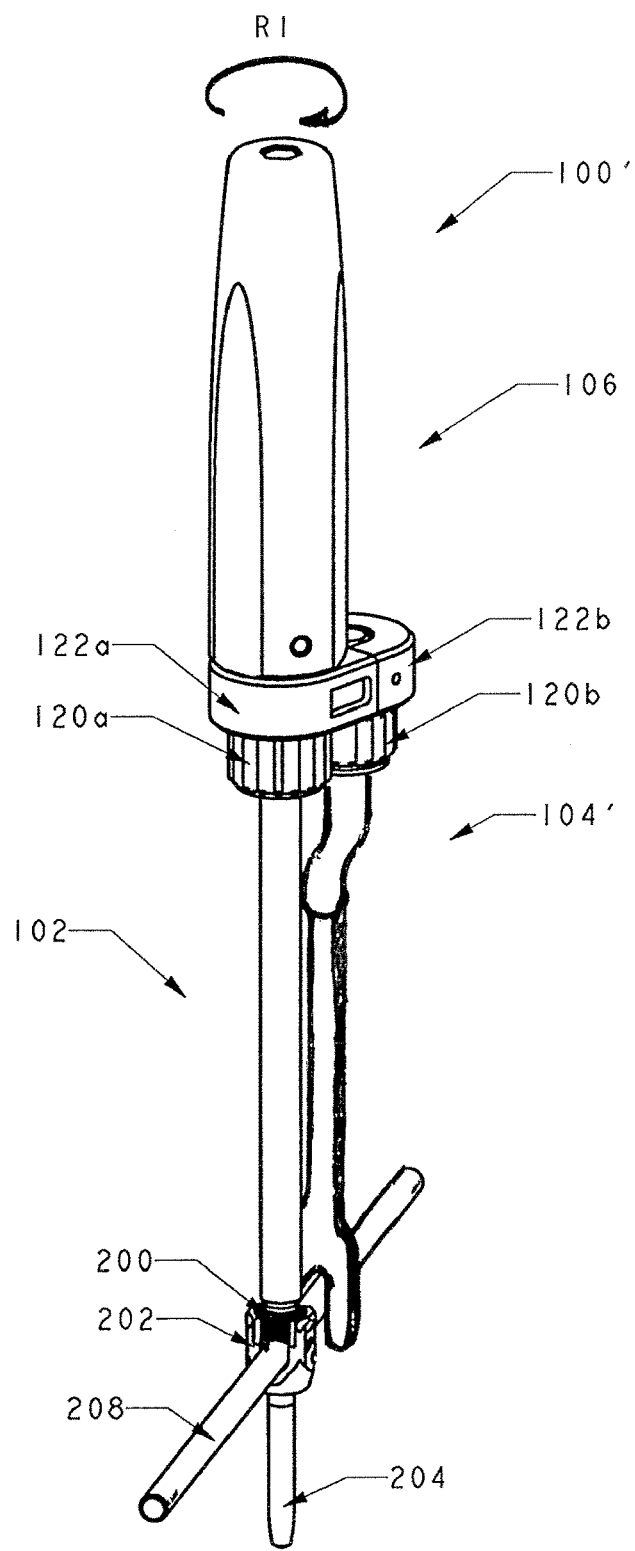

SURGICAL DEVICES AND METHODS FOR DRIVING AN IMPLANT AND APPLYING COUNTER TORQUE

CROSS-REFERENCE TO RELATED APPLICATIONS

This application is a continuation of U.S. application Ser. No. 14/746,985 filed on Jun. 23, 2015, which is hereby incorporated by reference herein.

FIELD

The present disclosure relates to surgical devices and methods for driving an implant, such as a spinal implant, and applying counter torque.

BACKGROUND

In various surgical procedures, one implant can be secured relative to another implant and/or to an anatomical structure. For example, spinal fixation procedures can be performed to align and/or fix desired relationships between adjacent vertebrae and can utilize multiple implants. Spinal fixation procedures typically include positioning a plurality of spinal fixation assemblies within target vertebrae, each fixation device typically having a threaded shank portion configured to be disposed (e.g., threaded) within a vertebra and a proximal receiver head configured to receive and secure some type of spinal stabilization element (e.g., a rigid or flexible rod, a cable, a biological construct, a tether, a tape, etc.). Once these assemblies are disposed within the target vertebrae, a spinal stabilization element or rod can be positioned and secured within the receiver heads such as by rotating a driver to fix a locking element within the receiver head. Once secured as such, the installed spinal stabilization rod can hold the vertebrae in the desired spatial relationship, either until desired healing or spinal fusion has taken place, or for some longer period of time.

While a driver can be configured to advance the locking element within the receiver head, fixing the stabilization element therein, a user can encounter some difficulties. For example, when using a driver, it can be difficult to apply the rotational forces to the implant rather than to the anatomy. As the driver is rotated to advance the locking element in a receiver member of a fixation assembly, the locking element resists and the driver can unintentionally apply a force that tends to rotate the target vertebrae rather than rotate the locking element into and relative to the receiver member. During rotation of the implant, a counter torque can be applied relative to the implant to avoid this undesirable rotational force being applied to the vertebrae and instead apply the rotational force to the implant so that it can rotate relative to one or more other implants.

Conventional drivers can include counter torque features, but also have various deficiencies. For example, some drivers utilize first and second handles that are angularly offset and obstruct the view of the implant. In one such device, the first handle can be coupled to a sleeve and the second handle can be coupled to a shaft received in the sleeve such that rotating the shaft within the sleeve drives the implant. However, this configuration increases the size of the sleeve's diameter because it must be large enough to accommodate the shaft. This can make it difficult for a user to visually monitor the driving progress and can increase trauma by requiring larger incisions to accommodate the driver. Additionally, a user must use both hands to operate the driver, crowding the operating space and leaving the user with no free hands. Still further, if the distal end of the driver is offset from and improperly aligned with a mating feature formed in the screw, rotating the driver may strip the screw head and the screw must be removed and replaced before the procedure can continue, thereby increasing the duration of the surgical procedure and the associated risks to the patient.

Thus, there remains a need for surgical devices and methods for driving an implant and applying counter torque.

SUMMARY

Devices, systems, and methods are provided for rotatably driving an implant and applying a counter torque. The devices herein can have various features that facilitate application of a counter torque as the device drives an implant relative to a patient's body. For example, a driver can include a drive shaft and counter torque shaft configured to couple to a handle. A distal end of each of the first and second shafts can have a mating tip selected to mate with a specific type of implant (such as a locking screw or a fixation rod of a spinal fixation assembly) and/or to mate with a patient's anatomy. This can allow the driver to be used in various types of surgical procedures that utilize multiple types of implants, such as procedures to align and/or fix desired relationships between adjacent vertebrae. To further accommodate different surgical sites and procedures, the shafts of the device can be removed and replaced from the handle as desired, allowing a user to select shafts having particular lengths and/or particular distal mating tips. A housing can contain drive mechanisms such as gears which allow the drive shaft to rotate in a first direction and cause the counter torque shaft to tend to orbit around the driver shaft. In use, rotating the handle can cause the distal mating tip of the driver shaft to rotate in a first direction, driving the implant, and this can cause the counter torque shaft to try to orbit around the driver shaft. However, when the counter torque shaft is orbitally constrained relative to the implant such that the counter torque shaft cannot orbit around the driver shaft and the implant, this restriction of the orbiting force applies the counter torque.

In some embodiments, a driver configured to apply a counter torque includes a handle configured to be grasped by a user, a driver shaft having a proximal end coupled to the handle and a distal end configured to mate with an implant, a counter torque shaft having a proximal end coupled to the handle, and a drive mechanism including first and second gears. The first gear can be configured to rotate with the handle and the first and second gears can be in mesh. In use, rotating the handle can rotate the driver shaft and the first gear in a first direction, thereby rotating the second gear in a second direction that is opposite to the first direction such that when the counter torque shaft is orbitally constrained relative to the driver shaft, the counter torque shaft applies a counter torque.

The device can vary in any number of ways. For example, the first and second gears can have a gear ratio of 1:1. The shafts and the handle of the device can also vary. A longitudinal axis of the driver shaft can be laterally offset from a longitudinal axis of the counter torque shaft. A longitudinal axis of the handle can be coaxial with the longitudinal axis of the drive shaft. The relative length of the shafts can vary. For example, a proximal-to-distal length of the drive shaft can be less than or equal to a proximal-to-distal length of the counter torque shaft. A distal end of the counter torque shaft can include a recess configured to be positioned around a portion of a stabilization element. The counter torque shaft can include at least one curve or bend proximal to its distal end to decrease a width between an outermost surface of the driver shaft and an outermost surface of the counter torque shaft.

A system configured to apply a counter torque as an implant is rotated can include a driver and an implant. The driver can include a driver shaft having a proximal end and a distal mating tip, a counter torque shaft having proximal and distal ends, a handle configured to receive a proximal end of the driver shaft, a first drive mechanism coupled to the driver shaft and a second drive mechanism coupled to the counter torque shaft. The driver can further include a connector having first and second connector members, the first connector member being disposed along the handle and the second connector member being laterally offset from the handle and coupled to the counter torque shaft. The implant can be part of a spinal fixation assembly and the implant can couple to the distal mating tip of the driver. When the distal mating tip of the driver is coupled to the implant, rotating the handle can rotate the first drive mechanism in a first direction, rotating the second drive mechanism in a second, opposite direction such that when the counter torque shaft is orbitally constrained relative to the spinal fixation assembly, a counter torque is applied.

The system can vary in any number of ways. The first connector member can include a first mating feature and the second connector member can include a second mating feature such that the first and second connector members are detachable from one another. The handle can have at least one groove formed in an outer surface thereof and sized and shaped to receive a portion of the first connector member. The handle can include a releasable mechanism that holds the driver shaft in the handle and that can be selectively released to allow the driver shaft to be removed and replaced, such as a ball plunger. The second drive mechanism can be configured to rotate relative to the counter torque shaft. In some embodiments, the implant is a set screw. The system can further include a housing adjacent to the handle and containing the drive mechanism, and the housing being removable from the driver.

In some embodiments, a method of driving an implant in a first direction and applying a counter torque in a second, opposite direction includes engaging a first implant with a distal tip of a driver shaft of an instrument, the instrument having a handle at its proximal end, positioning a counter torque shaft of the instrument adjacent to at least one of a second implant and an anatomical structure such that the counter torque shaft is orbitally fixed, and rotating the handle to rotate the drive shaft in a first direction which causes the counter torque shaft to orbit in the second direction, thereby applying a counter torque and driving the implant distally.

The method can vary in any number of ways. For example, rotating the handle can include manually rotating the handle or activating a power source that rotates the handle. A spinal stabilization element can be positioned within at least one receiver member prior to engaging the first implant with the distal tip of the driver shaft. Positioning the counter torque shaft can include coupling a distal end of the counter torque shaft to a spinal stabilization element such that the counter torque shaft is orbitally fixed relative to the stabilization element. The method can include releasing the counter torque shaft from the instrument, engaging the implant with the distal tip of the driver shaft, and rotating the driver shaft without applying a counter torque via the counter torque shaft.

The present invention further provides devices and methods as claimed.

BRIEF DESCRIPTION OF THE DRAWINGS

The invention will be more fully understood from the following detailed description taken in conjunction with the accompanying drawings, in which:

FIG. 1 is a perspective view of a driver that can apply a counter torque;

FIG. 2A is a cross-sectional view of the driver of FIG. 1 taken along a longitudinal axis of the driver;

FIG. 2B is an exploded perspective view of the driver of FIG. 1;

FIG. 3A is a perspective view of a first connector;

FIG. 3B is a perspective view of a second connector;

FIG. 3C is a sectional isometric view of the first and second connectors mated together with the handle not shown;

FIG. 5A is an isometric view of a counter torque shaft having a blunt distal tip;

FIG. 5B is a perspective view of a driver having a driver shaft and the counter torque shaft of FIG. 5A, the counter torque shaft being positioned near an implant;

FIG. 6A is a perspective view of a driver having a counter torque shaft that can engage an implant;

FIG. 7 is a perspective view of an exemplary driver having a second handle that can be grasped by a user to gain additional leverage when rotating the driver;

FIG. 10 is a perspective view of another exemplary driver having a counter torque shaft that locks onto a stabilization element.

DETAILED DESCRIPTION

Figure 4A:
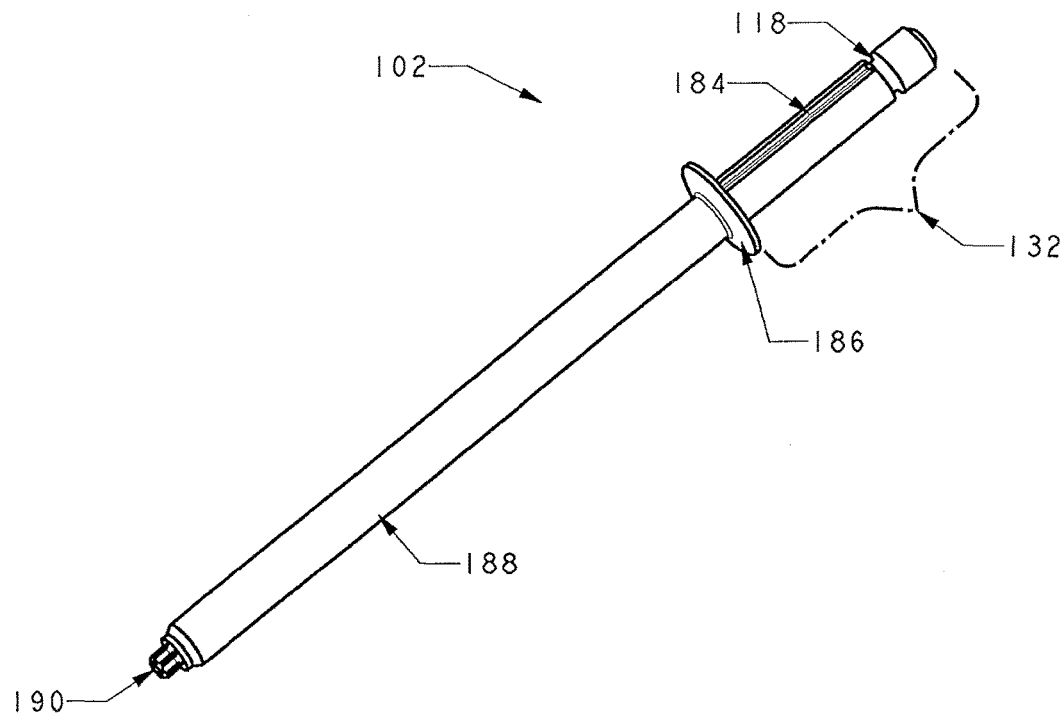
FIG. 4A is an isometric view of a driver shaft having a first type of distal mating tip.

Devices, systems, and methods are provided for rotatably driving an implant and applying a counter torque. The devices herein can have various features that facilitate application of a counter torque as the device drives an implant relative to a patient's body. For example, a driver can include a drive shaft and counter torque shaft configured to couple to a handle. A distal end of each of the first and second shafts can have a mating tip selected to mate with a specific type of implant (such as a locking screw or a fixation rod of a spinal fixation assembly) and/or to mate with a patient's anatomy (such as a vertebra). This can allow the driver to be used in various types of surgical procedures that utilize multiple types of implants, such as procedures to align and/or fix desired relationships between adjacent vertebrae. To further accommodate different surgical sites and procedures, the shafts of the device can be removed and replaced from the handle as desired, allowing a user to select shafts having particular lengths and/or particular distal mating tips. A housing can contain drive mechanisms such as gears which allow the drive shaft to rotate in a first direction and cause the counter torque shaft to want to orbit around the driver shaft. In use, rotating the handle can cause the distal mating tip of the driver shaft to rotate in a first direction, driving the implant, and this can cause the counter torque shaft to try to orbit around the driver shaft. However, when the counter torque shaft is orbitally constrained relative to the implant such that the counter torque shaft cannot orbit around the driver shaft, this restriction of the orbiting force applies the counter torque.

A surgical procedure can be performed on a spine such as a fixation or stabilization procedure utilizing multiple implants, and one or more of the implants can be rotatably driven into the patient. Such spinal fixation procedures typically include positioning a plurality of spinal fixation assemblies within the target vertebrae. These assemblies can include a fixation element having a threaded shank portion configured to be disposed within a vertebra and a proximal receiver head configured to receive and secure some type of spinal stabilization element (e.g., a rigid or flexible rod, a cable, a biological construct, a tether, a tape, etc.). The stabilization element or rod can be positioned and secured within the receiver heads in various ways, such as via one or more locking elements that can be driven into the receiver head using any of the drivers herein. For example, the distal mating tip of the driver can mate with the implant, e.g., the locking element, and the handle of the driver can be rotated to rotate the drive shaft. This can rotatably advance the locking element within the receiver head to lock the stabilization element therein. During manual or powered rotation of the driver, distal ends of the driver and the counter torque shaft can be axially and orbitally constrained relative to the implant (the driver shaft being in a constrained position when it is mated with the implant and the counter torque shaft being in a constrained position by anatomy and/or by one or more components of the spinal fixation assembly). With the shafts so positioned, the shafts cannot orbit relative to one another and the driver shaft rotates in a first direction to rotatably drive the implant. This can cause the counter torque shaft to tend to orbit around the driver shaft in an opposite direction as the rotation of the handle, but the counter torque shaft cannot because it is constrained by an implant or anatomy blocking its path. This restriction of the orbiting force can apply the counter torque.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

FIG. 1 illustrates an exemplary embodiment of a device that can be used to drive an implant and to simultaneously apply a counter torque. The device 100 can include a driver shaft 102, a counter torque shaft 104, a handle 106, and a housing 108. The handle 106 can have an elongate shape configured to be grasped by a user. The driver shaft 102 and the counter torque shaft 104 can be positioned side-by-side relative to one another, i.e., the counter torque shaft 104 can be laterally offset from the driver shaft 102 such that the counter torque shaft 104 does not contact or otherwise interfere with rotation of the driver shaft 102. The housing 108 can contain various drive mechanisms (not shown) which facilitate application of a counter torque as the driver shaft 102 drives the implant. The handle 106 and the driver shaft 102 can be configured to rotate as a unit such that when a distal end of the driver shaft 102 is mated with an implant and a distal end of the counter torque shaft 104 is in an axially fixed and orbitally constrained position such that the counter torque shaft 104 cannot orbit around the driver shaft 102, rotating the handle 106 both rotates the driver shaft 102 and operates the drive mechanism. The housing 108 can be shaped in various ways, but in the illustrated embodiment has a frustoconical shape.

The handle can have various sizes, shapes, and configurations. As shown, the handle 106 can have a cylindrical shape and can be tapered in a distal-to proximal direction to facilitate comfortable grasping by a user. The handle 106 can include one or more features that increase friction between the handle 106 and a user's hand, such as one or more planar surfaces 110 formed on and spaced apart around a circumference of the handle 106 shown in FIG. 1. The handle 106 need not include a taper and the handle 106 can be shaped in other ways that facilitate grasping by a user, such as T-shaped. If desired, a power source can be operatively coupled to the driver shaft 102 through the handle 106 to permit powered rotation of the handle 106. For example, a proximal end 106$p$ of the handle 106 can include one or more features that can mate with a drive shaft (not shown) connected to a power source (not shown) to permit powered rotation of the handle 106, such as a drive shaft mating recess 112. The handle 106 can further include a torque limiter configured to limit torque applied by the driver to a maximum torque (such as a torque of 8 Nm or less) to prevent the device from over tightening an implant.

FIGS. 2A and 2B illustrate components of the device of FIG. 1 in greater detail. FIG. 2A is a cross-sectional view of the device of FIG. 1 taken along a longitudinal axis $L_D$ of the handle 106/driver shaft 102 with the housing 108 removed from the device 100 to show some of the connections between the components in more detail. As shown, a proximal portion 114 of the driver shaft 102 can be received in the handle 106 such as in a channel 117 formed in the handle 106 and extending along the longitudinal axis $L_D$. Various mechanisms can be incorporated into the handle 106 that can allow it to hold the driver shaft 102 therein and that can be selectively released so that a user can remove the driver shaft 102 from the handle 106 as desired, such as a ball plunger, donut spring, etc. FIG. 2A illustrates an exemplary locking mechanism 116 that engages a recess or groove 118 formed around the driver shaft 102. As will be appreciated, the driver shaft 102 and the counter torque shaft 104 can be positioned in a specific orientation relative to one another. For example, a longitudinal axis of the counter torque shaft $L_C$ can be laterally offset from the longitudinal axis $L_D$ of the handle 106, and the device 100 can include one or more features that hold the counter torque shaft 104 in this position relative to the handle 106, as described in more detail below.

FIG. 2B illustrates an exploded view of the device of FIG. 1, including a drive mechanism and first and second connector members that hold the counter torque shaft 104 in the laterally offset position relative to the handle 106 and the driver shaft 102. Beginning with components directly coupled to the handle 106, the device 100 can include a first drive mechanism 120a, e.g., a first gear, which allows a torque to be transferred from the handle 106 to the counter torque shaft 104. The first gear 120a can be positioned at a distal end of the handle and can be coupled to the handle 106 using various mating techniques known in the art. As will be appreciated, the first gear 120a can be integrally formed on the handle 106 and/or can be mated thereto such that the handle 106 and the first gear 120a rotate together as a unit. One or more features on the handle 106 can mate with first connector member 122a. For example, the handle 106 can have one or more grooves, recesses, or stepped portions sized, shaped, and configured to receive the first connector member 122a. In the illustrated embodiment, the handle 106 includes first and second stepped portions 124, 126 that can seat the first connector member 122a and that each have a smaller diameter than a proximal portion of the handle 106 that is grasped by a user. The stepped portions 124, 126 can define a distal-facing surface 128 that can act as an automatic stop for the first connector member 122a when the first connector member 122a is positioned on the handle 106. The stepped portions 124, 126 can have a substantially circular cross-sectional shape taken along a plane perpendicular to the longitudinal axis $L_D$ of the handle 106. The stepped portions 124, 126 can be shaped in other ways, such as rectangular, elliptical, hexagonal, etc. The handle 106 and the first gear 120a can have features that allow the driver shaft 102 to selectively couple to the handle 106. For example, the first gear 120a can have a central opening 130 that is in communication with the channel (not shown) formed in the handle 106 to allow a proximal portion 132 of the driver shaft 102 to extend through the opening 130 and into the channel.

A second connector member 122b can be attached to the first connector member 122a and can receive and can hold the counter torque shaft 104 in the laterally offset position. Similar to the first gear 120a, second gear 120b can have a central opening formed therein that allows proximal portion of the counter torque shaft 104 to be inserted therethrough. The second connector member 122b can have an opening formed therein having a locking feature 116b that is sized, shaped, and configured to hold a proximal end of the counter torque shaft 104 in a fixed relationship relative to the second connector member 122b. This locking feature can interact with a corresponding locking feature formed on a proximal end 104p of the counter torque shaft 104, such as circumferential groove 138 shown in FIG. 2B. As will be appreciated, the second connector 122b can include any locking feature known in the art such as a dowel pin, snap ring, bull plunger, etc. The counter torque shaft 104 can be rotatably or non-rotatably coupled to the second connector member 122b, that is, the counter torque shaft 104 can be independently rotatable relative to the second gear 120b and the second connector member 122b or can be configured to rotate as a unit with the second gear 120b. In a first embodiment, when the counter torque shaft 104 extends through the first gear 120a and is locked to the second connector member 122b, rotating the first gear 120a can rotate the second gear 120b without causing the counter torque shaft 104 to rotate. This rotatable coupling can reduce the risk of trauma on the patient and can reduce friction between the counter torque shaft 104 and other implants.

The rotatable coupling can be accomplished in various ways, such as by coupling a proximal portion 142 of the counter torque shaft 104 to the second connector member 122b while leaving a gap between a proximal surface 140 of the second gear 120b and a distal surface 141 of the second connector member 122b. A washer (not shown) can be positioned in the gap to decrease friction between the member 122b and the second gear 120b. Alternatively, the counter torque shaft 104 can be configured to rotate as a unit with the second gear 120b.

The drive mechanism of the driver can vary. More specifically, the first gear 120a and the second gear 120b can have any number of teeth formed on their outer surfaces. The first and second gears can have the same number of teeth such that rotation of the first gear 120a causes a corresponding rotation of the second gear 120b without mechanical advantage, as in the illustrated devices. In other embodiments, the first 120a and second gears 120b can have different numbers of teeth such that a mechanical advantage is generated via rotation of the gears 120a, 120b.

The first connector member 122a can have various sizes, shapes, and configurations. As shown in FIG. 3A, the first connector member 122a can have a lateral opening 144 formed therein for receiving a portion (not shown) of the second connector member 122b. The first connector member 122a can have a superior face 146 and an inferior face 148 and an opening 150, 152 formed through each of the superior and inferior surfaces 146, 148. The openings 150, 152 can be sized and shaped to allow the first gear 120a of the handle 106 to pass therethrough. As will be appreciated, the openings 150, 152 can be shaped in various ways such as circular, elliptical, rectangular, hexagonal etc. In the illustrated embodiment, the openings 150, 152 are circular shaped and an inner diameter of the openings are greater than an outer diameter of the first gear 120a (where the outer diameter of the first gear 120a includes the teeth of the gear). The superior and inferior faces 146, 148 can be shaped in various ways. For example, the superior and inferior faces 146, 148 can each have first edges 154, 156 that are curved and a first lateral face 158 that connects the edges 154, 156 and is substantially perpendicular to the superior and inferior faces 146, 148. In the illustrated embodiment, the radius of curvature of the edges 154, 156 can be equal to a radius of curvature of the proximal portion of the handle 106 that is grasped by a user. As a result, when the first connector 122a is coupled to the handle 106, the first edge 154 can be flush or semi-flush with the proximal portion of the handle 106. The inferior and superior faces 146, 148 of the first connector member 122a can define a second lateral face 160 on an opposite end thereof that is configured to mate with a corresponding lateral face of the second connector member 122b (not shown). While the second lateral face 160 can be shaped in various ways, in the illustrated embodiment the second lateral face 160 is perpendicular to a longitudinal axis of the openings 150, 152 and is defined by four substantially straight edges 160a, 160b, 160c, 160d. The edges 160a, 160b, 160c, 160d can be coupled to the superior and inferior faces 146, 148 and can define the lateral opening 144 which extends substantially perpendicular to longitudinal axis of the openings 150, 152 which receive the first gear 120a. The first connector member 122a can include one or more locking features configured to selectively mate with the second connector member 122b, such as first and second tabs 162a. 162b. The first and second tabs 162a, 162b can be opposed, i.e., formed on opposed ends of the first connector member 122a, each of the tabs 162a, 162b being adjacent to the lateral opening 144. In the illustrated embodiment, the tabs 162a, 162b can be rectangular shaped, but the tabs 162a, 162b can be shaped in other ways. The tabs 162a, 162b can be defined by openings 164a, 164b, 164c formed in the first connector member 122a along all or part of the perimeter of the tabs 162a, 162b, such as along superior, inferior, and lateral edges of the tabs 162a, 162b and this can allow the tabs 162a, 162b to flex inwardly and outwardly relative to the lateral face 158 similar to a spring. An inner surface of each tab 162a, 162b can include a stop 165, 167 formed on a second lateral edge thereof furthest away from the lateral opening 144. This stop can provide tactile and/or auditory feedback to a user when the second connector member 122b is in the desired locked position relative to the first connector member 122a. An inner surface of each tab 162a, 162b can include a protrusion 168 formed on its first lateral edge closest to the lateral opening 144 that can also facilitate locking the connector members 122a, 122b.

FIG. 3B shows an isometric view of the second connector member 122b. The second connector member 122b can include a body 170 that receives the counter torque shaft 104 and an extension 172 configured to be inserted into the lateral opening 144 in the first connector member 122a. The body 170 of the second connector member 122b can have a semi-circular cross-sectional shape taken along an axis perpendicular to the longitudinal axis $L_D$ of the handle 106. The body can have a lateral surface 173 with the same radius of curvature as the curved lateral face 158 of the first connector member 122a as shown, or the lateral surface 173 can be shaped in other ways. A central opening 176 can be formed in the body 170 of the second connector member 122b for receiving the proximal end 104p of the counter torque shaft 104 and as previously mentioned, the opening 176 can lock the counter torque shaft 104 therein. The extension portion 172 can have one or more surfaces selected to mate with a portion of the handle 106, e.g., a shape of one or more inner surfaces of the extension portion 172 can correspond to a shape of the grooves/stepped portions on the handle 106. In the illustrated embodiment, the extension portion 172 of the second connector member 122b has a semi-circular, concave first inner surface 174 that extends between and connects first and second arms 178a, 178b. A superior inner surface 180 and inferior inner surface (not shown) can be disposed above and below the first inner surface 174 and can include a central circular portion 180c and first and second straight lateral portions 180a, 180b. The first inner surface 174 and the superior and inferior inner surfaces of the extension portion 172 can mate with the first and second stepped portions 124, 126 on the handle 106 and the first and second arms 178a, 178b can be positioned around an outer surface of the stepped portions 124, 126 to help lock the connector members 122a, 122b. The connector members 122a, 122b can include other locking features. For example, first and second grooves 182a, 182b can be formed in each of the first and second arms 178a, 178b of the extension portion 172 and the grooves can extend in superior to inferior direction to facilitate locking the first and second connector members 122a, 122b. More specifically, as the second connector member 122b is inserted into the first connector member 122a, each of the grooves 122a, 122b can receive a leading edge of the corresponding tabs 162a, 162b and flexing of the tabs 162a, 162b and the protrusion 168 on the tabs 162a, 162b can compress around the respective grooves 182a, 182b and apply a locking force. This force can be sufficient to hold the connector members 122a, 122b together, while still allowing for a user to selectively, manually separate the connector members 122a, 122b.

FIG. 3C shows the first and second connector members 122a, 122b coupled together in a mated configuration. The extension portion 172 of the second connector member 122b can be inserted into the lateral opening 144 formed in the first connector member 122a. With the second connector member 122b so positioned, the groove on each of the arms of the second connector member 122b can deform the respective tab 162a, 162b on the first connector member 122a outwardly and the tabs 162a, 162b can be seated in the superior-to-inferior grooves 182a, 182b formed in the extension portion 172 and this can apply an additional locking force. The locking force between the first and second connector members 122a, 122b can also facilitate maintaining the first and second gears 120a, 120b in mesh, as shown. To release the first and second connector members 122a, 122b, a user can grasp the connector members 122a, 122b and apply a separating force to the connector members 122a, 122b that releases the protrusions from the grooves and separates the connector members 122a, 122b.

Figure 4B:
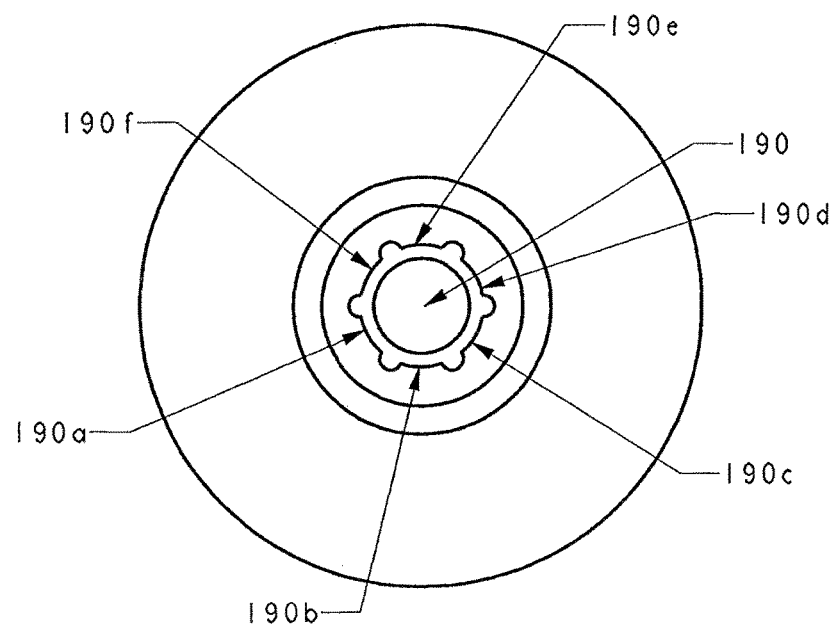
FIG. 4B is an end view of the distal mating tip of FIG. 4A.

FIGS. 4A and 4B illustrate the driver shaft 102 in more detail. The driver shaft 102 can include various features to allow the shaft 102 to mate with an implant (not shown) and to allow the driver shaft to mate with the first gear 120a and the handle 106. The proximal portion 132 of the driver shaft 102 can include the circumferential groove 118 formed in an outer surface thereof that can assist with locking the driver shaft 102 to the handle 106. The proximal portion 132 of the driver shaft 102 can further include one or more features that allow the drive shaft 102 to rotate with the handle 106. For example, the drive shaft 102 can have a longitudinal extension 184 extending in a proximal-to-distal direction which can be received in the corresponding longitudinal recess formed in the handle (not shown). This can key the driver shaft 102 to the handle 106 such that the rotating the handle 106 causes corresponding rotation of the driver shaft 102. The driver shaft 102 can include a stop member 186 formed on an outer surface thereof for holding the first gear 120a in a fixed axial position on the driver shaft 102. In the illustrated embodiment, the stop member 186 is disc-shaped but the stop member 186 can be shaped in other ways and can be integrally formed on the shaft (such as molded thereto) or can be coupled to the shaft 102 using any techniques known in the art. The stop member 186 can be positioned along the driver shaft 102 so that when the proximal portion 132 of the driver shaft 102 is disposed in the handle 106, the stop member 186 is adjacent to a distal surface of the first gear 120a. A second, distal portion 188 of the driver shaft 102 can have any longitudinal length and the length can be selected for a particular surgical procedure. The driver shaft 102 can be adjustable and can include various features to allow a user to selectively increase and/or decrease its length. The driver shaft 102 can be generally elongate and can have by way of non-limiting example, a circular, elliptical, or hexagonal cross-sectional shape. The distal portion 188 driver shaft 102 can be cylindrical shaped and can have a distal mating tip 190 configured to mate with a particular type of implant (not shown). The distal mating tip 190 can be shaped in various ways, but can generally be configured to mate with a corresponding recess formed in an implant (such as a recess having an identical shape as the distal mating tip). As shown in FIG. 4B, in one embodiment the distal mating tip 190 can be hexagonal shaped and can have six sides 190a, 190b, 190c, 190d, 190e, 190f such that the distal mating tip 190 can mate with an implant having a corresponding hexagonal shaped recess formed therein. In some embodiments, the distal mating tip 190 can be selectively removed and replaced from the driver shaft 102 and/or the distal mating tip 190 can be integrally formed on the handle 106.

FIGS. 5A and 5B illustrate the counter torque shaft 104 that couples to the second connector member 122b in greater detail. The counter torque shaft 104 can include various features to allow the counter torque shaft 104 to couple to the second connector member 122b. Similar to the driver shaft 102, proximal portion 132 of the counter torque shaft 104 can include a circumferential groove 118 formed in an outer surface thereof that can assist with locking the counter torque shaft 104 on the second connector member 122b. The counter torque shaft 104 can include a stop member 186 formed on an outer surface thereof for holding the second gear 120b in a fixed axial position thereon. In the illustrated embodiment, the stop member 186 is disc-shaped but can be shaped in other ways and can be integrally formed on the shaft 104 (such as molded thereto) or can be coupled to the shaft 104 using any techniques known in the art. The stop member 186 can be positioned along the shaft 104 so that when the proximal portion 132 of the counter torque shaft 104 is coupled to the second connector member 122b, the stop member 186 is adjacent to a distal surface of the second gear 120b. A second, distal portion 188 of the counter torque shaft 104 can have any longitudinal length and the specific length can be selected by a user for a particular surgical procedure. The counter torque shaft 104 can further be adjustable and can include various features to allowing a user to selectively increase and/or decrease its length and the length of the distal portion 188. The counter torque shaft 104 can be cylindrical shaped along its length and in some embodiments, can have a blunt distal tip 190. In general, the distal end can be blunt, spherical, or otherwise shaped to be atraumatic to tissue. In the illustrated embodiment, the distal mating tip 190' has a hemi-spherical distal tip 190r' that is atraumatic to tissue. FIG. 5B illustrates device 100 including the driver shaft 102 and the counter torque shaft 104 and the first and second gears 120a, 120b held in mesh by the first and second connector members 122a, 122b. As shown, the distal mating tip 190 of the driver 102 is mated to a set screw 200 of a receiver head 202 attached to a spinal fixation element, e.g. a bone anchor 204.

A counter torque shaft can vary and can have other distal tips, such as a distal mating tip 190' sized, shaped, and configured to mate with and engage an implant such as a spinal stabilization element. The distal mating tip 190' of the counter torque shaft 104' can engage with and surround the stabilization element such that the counter torque shaft 104' cannot move laterally relative to the stabilization element and cannot orbit around the driver shaft 102. In the embodiment of FIG. 6A, the distal mating tip 190' includes first and second arms 193', 195' which define a seat therebetween. The arms 193', 195' can be sized and spaced at a selected distance apart such that the arms 193', 195' can hold a stabilization element in the seat. In the illustrated embodiment, the first and second arms 193', 195' of the distal mating tip 190' can contact and hold lateral surfaces of the rod 208 and can define a space 197' between a superior surface of the rod 208 and the distal mating tip 190' to allow the counter torque shaft 104' to move distally when the driver shaft 102 moves distally during tightening of the implant.

Figure 6B:
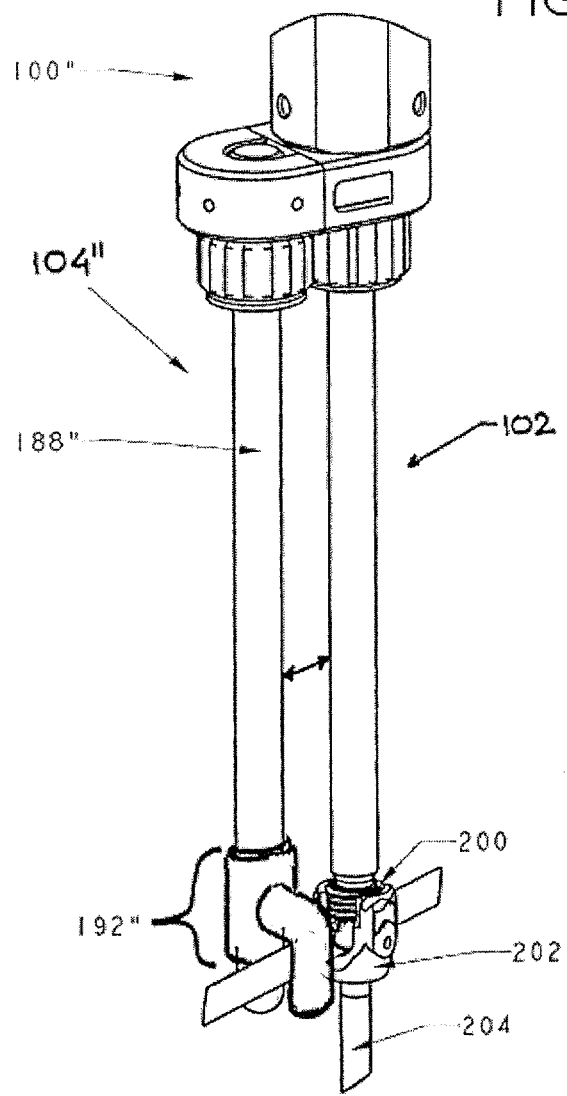
FIG. 6B is a perspective view of a driver having another exemplary counter torque shaft that can engage an implant.

A shape and size of the counter torque shaft can be varied to decrease a size profile of the device and allow the device to be more readily used in surgical sites having multiple implants and/or having anatomy that leaves only a small available space for the shafts. FIG. 6B illustrates a device 100 that includes the driver shaft 102 and another exemplary counter torque shaft 104". The portion of the counter torque shaft 188" is laterally offset from the driver shaft 102, as in other embodiments, but a distal portion 192" of the counter torque shaft 104" is contoured and follows a shape of an outer surface of an implant, e.g., the receiver head 202. The counter torque shaft can be curved or can include one or more bends formed therein that allow the curved distal portion 192" of the counter torque shaft 104" to accommodate and be positioned adjacent to the receiver head 202 without contacting the receiver head 202 and can allow the counter torque shaft 104" to engage a rod as in the previous embodiment. The curved distal portion 192" can be selectively mated to and removed from the counter torque shaft 104" similar to the other described mating tips. As will be appreciated, the counter torque shaft 104" can include any of the features of the other counter torque shafts 104, 104' described above, such as a distal mating tip having a preformed curved configuration and/or a distal mating tip that can be selectively attached to a preformed curved or bent shaft.

As shown in FIG. 7, a driver device can include a second handle 206 in addition to the first handle 106. In general, the second handle 206 can be selectively grasped to allow the user to gain additional leverage and/or stability when rotating the first handle 106. The second handle 206 can have various sizes, shapes, and configurations, and can be coupled to one or more components of the device. For example, a connecting arm 208 can couple the second handle 206 to a portion of the second connector member 122b, e.g., the superior surface of the second connector member 122b. The connecting arm can be integrally formed with the second handle 206 and the second connector member 122b or coupled thereto using any mating technique known in the art. The second handle 206 can be disposed at an angle relative to the first handle (i.e., a longitudinal axis Ls of the second handle 206 can be angled relative to the longitudinal axis $L_D$ of the first handle 106) such that a user can grasp both handles 106, 206 and simultaneously rotate the first handle 106. In illustrated embodiment, the longitudinal axis Ls of the second handle 206 is substantially perpendicular to the longitudinal axis $L_D$ of the first handle 106.

Exemplary methods for driving an implant while applying a counter torque are also provided. The methods for driving an implant can differ from prior art methods at least because the driver can be operated using one hand. That is, the handle 106 can be grasped and manually rotated using one hand (although two hands can be used if desired).

Figure 8:
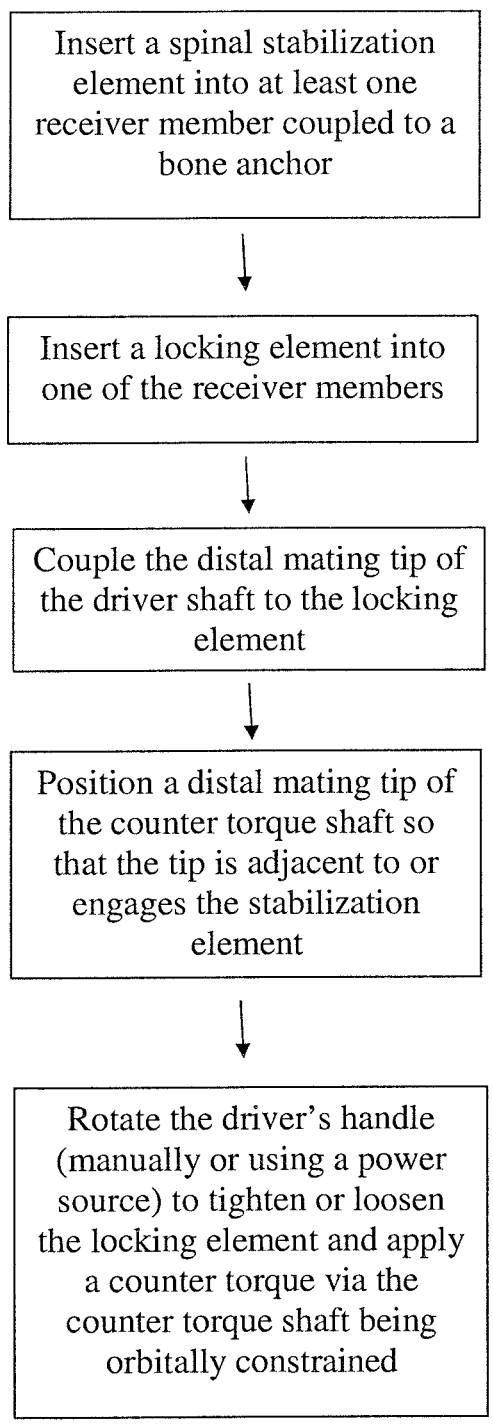
FIG. 8 is a flow chart of an exemplary method for driving an implant and applying a counter torque.

FIG. 8 is a functional diagram listing the steps of an exemplary method for driving an implant. As will be appreciated, the surgical procedure can be a minimally invasive or open procedure, and can be a robot-assisted procedure. One or more bone anchors can be rotatably driven and installed into a vertebra of a patient, and the vertebrae having the bone anchor(s) installed therein can be on adjacent levels or spaced apart across multiple levels of the spine. A receiver head can be coupled to one or more of the anchors using any technique known in the art and a spinal stabilization element, e.g., a spinal fixation rod, can be inserted through one or more of the receiver heads via known techniques. An implant, e.g., a set screw, screw, locking cap, can be positioned adjacent to a proximal end of the receiver head to prepare for rotatably driving the set screw into the receiver head to lock the spinal fixation rod therein.

Figure 9A:
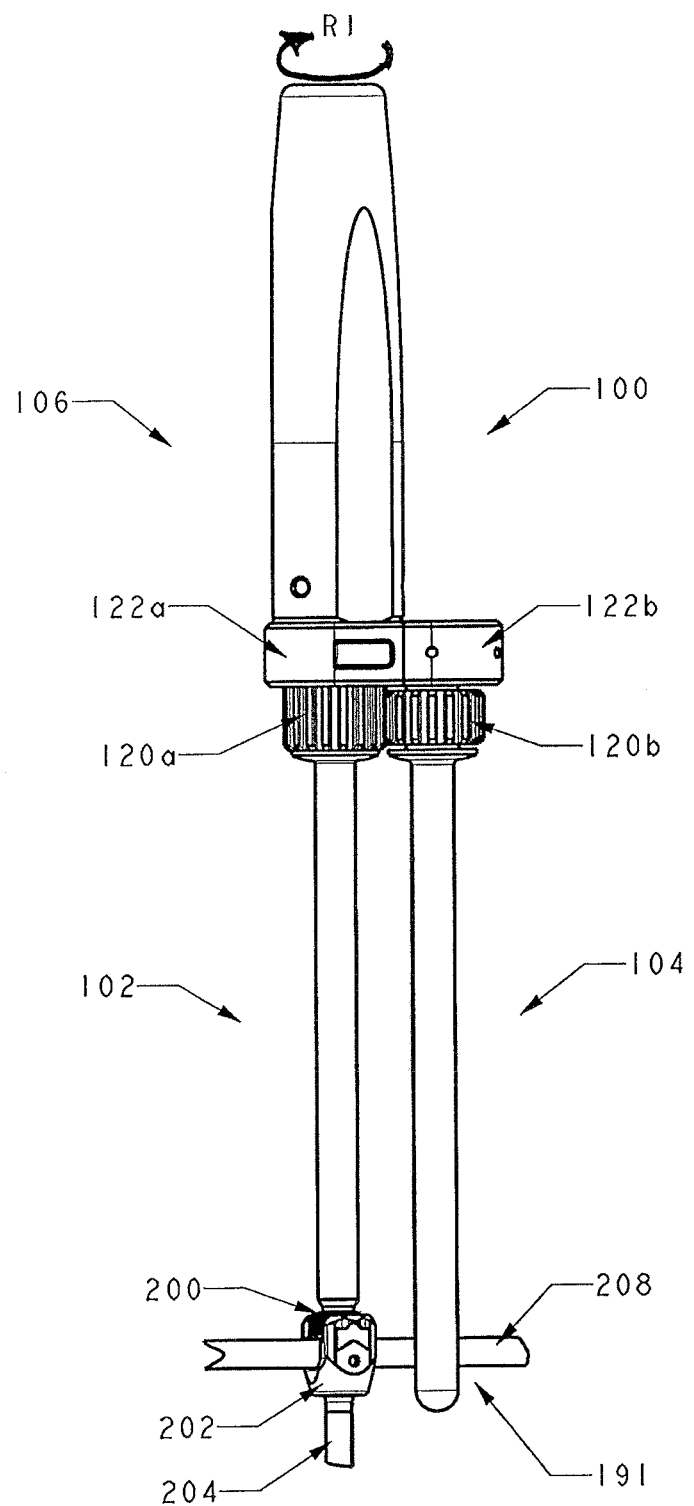
FIG. 9A is side view of an exemplary driver coupled to a locking element of a spinal fixation assembly and rotated in a clockwise direction, and having a counter torque that contacts and rests against a spinal stabilization element.
Figure 9B:
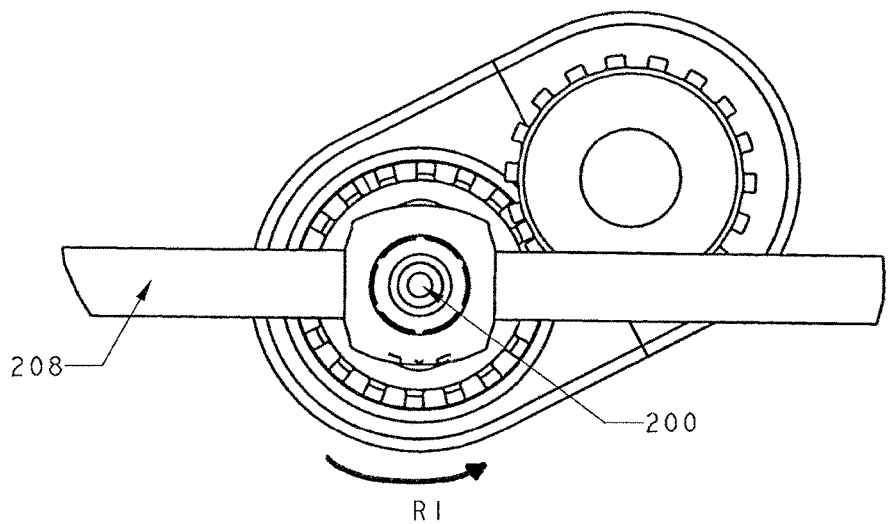
FIG. 9B is a bottom view of the locking element showing its direction of rotation (which is the same as the rotational direction of the handle)

While the method can be performed using a driver having the many variations of features described, a method for driving an implant is described in connection with the driver 100 shown in FIGS. 9A and 9B. With the set screw 200 positioned in the receiver head 202, the driver shaft 102 and the counter torque shaft 104 can be inserted into the patient, such as by inserting the shafts 102, 104 through a single incision or by inserting each shaft 102, 104 into a separate incision formed in the patient. The distal mating tip 190 of the driver 102 can couple to and be received in a mating recess (not shown) formed in the implant 200. The handle 106 and the shafts 102, 104 can be sized and shaped so as to not obstruct the user's view of the distal mating tip 190 of the driver shaft 102 and a distal tip 191 of the counter torque shaft 104. As a result, the user can closely monitor the position of the distal tips 190, 191 relative to an implant and/or the patient's anatomy and adjust the position of the distal tips 190, 191 as desired prior to or during driving of the implant 200. A user can also monitor the orientation of the shafts 102, 104 to ensure that the longitudinal axis of the handle 106 is axially aligned with a longitudinal axis extending through a center of the implant (e.g., the set screw 200) to ensure that rotation of the handle 106 does not strip or otherwise damage the implant 200.

Figure 9C:
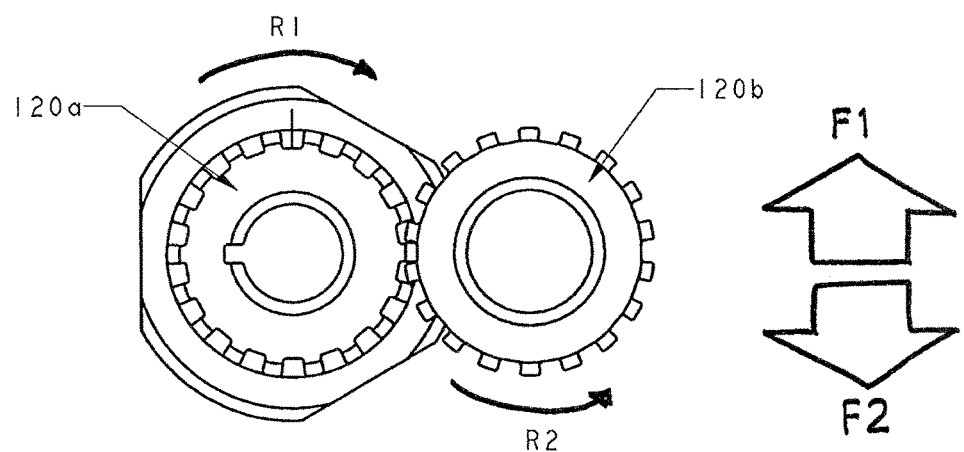
FIG. 9C is a top view of the drive mechanism of the driver of FIG. 9A showing the direction of rotation of the handle and the gears and resulting forces that are generated.

With the distal tip 190 of the driver shaft 102 positioned in the implant 200, the handle 106 can be rotated to change a position of the distal end 191 of the counter torque shaft 104 so that it contacts at least one of an anatomical structure or another implant, e.g., a spinal stabilization element 208. Because of friction between various components of the driver 100 (e.g., friction between the superior surface of the first connector member 122a and the distal-facing surface of the handle 106) this positioning step can be performed without causing the gears 120a, 120b of the drive mechanism to rotate. That is, a user can rotate the handle 106 in a desired direction (such as counter clockwise) which causes the second connector member 122b and the counter torque shaft 104 to move and swing together as a unit with the handle 106 until the distal end 191 of the counter torque shaft 104 contacts an anatomical structure/implant. With the counter torque shaft 104 so positioned, a user can rotate the handle 106 in a first direction (such as clockwise) or can activate a power source to begin rotating the handle 106 so as to overcome the friction between the handle 106 and the first connector member 122a and to begin driving the implant 200 distally within the receiver head 202. This can cause the first and second gears 120a, 120b to rotate. As shown in FIGS. 9B and 9C, clockwise rotation R1 of the first gear 120a will cause the second gear 120b to rotate R2 in a counter clockwise direction and in turn the second gear 120b and the counter torque shaft 104 will try to orbit around the first gear 120a in a counter clockwise direction with a force F1. However, the distal tip 191 of the counter torque shaft 104 is axially and orbitally constrained by an implant or anatomy which restricts the counter torque shaft 104 from orbiting around the driver shaft 102. At this time, the first and second connectors 122a, 122b are also in a constrained axial and rotational position and the second connector member 122b cannot orbit around the first connector member 122a in the counter clockwise direction. The anatomical structure/implant against which the counter torque shaft 104 is positioned (such as the spinal fixation element 208 or a vertebra) will apply an equal but opposite force F2 to the counter torque shaft 104. As implant 200 is driven into the receiver head 202, the rotational force/torque applied to the handle 106 is increased to counteract the resistance from the implant 200 and the counter torque force F1 applied by the counter torque shaft 104 and the constraining force F2 restricting the shaft 104 from orbiting also increases.

The method for driving an implant can also be performed using the driver 100' having the counter torque shaft 104' with the distal mating tip 190' that engages a particular type of implant, as in FIG. 10. The method can include the steps described above and when the set screw 200 is positioned in the receiver head 202, the driver shaft 102 and the counter torque shaft 104' can be inserted into the patient. This can be accomplished by inserting the shafts 102, 104' through a single incision or by inserting each shaft 102, 104' into a separate incision formed in the patient. The distal mating tip 190' of the driver 102 can couple to and be received in a mating recess (not shown) formed in the implant 200. As in the previous embodiment, the handle 106 and the shafts 102, 104" can be sized and shaped so as to not obstruct the user's view of the distal tips 190, 190' of the driver shaft 102 and of the counter torque shaft 104'. As a result, the user can closely monitor the position of the distal tips 190, 190' of the device 100' relative to an implant and/or the patient's anatomy and adjust the position of the distal tips 190, 190' as desired prior to or during the driving process. A user can also monitor the orientation of the shafts 102, 104' to ensure that the longitudinal axis of the handle 106 is axially aligned with a longitudinal axis extending through a center of the implant (e.g., the set screw 200) to ensure that rotation of the handle 106 does not strip or otherwise damage the implant 200.

With the distal tip 190 of the driver shaft 102 positioned in the implant 200, the handle 106 can be rotated (such as in a counter clockwise direction) to change a position of the counter torque shaft 104' relative to the set screw 200 so that the distal tip 190' of the counter torque shaft 104' can engage with and surround an implant such as the spinal fixation rod 208 such that the counter torque shaft 104' cannot move laterally relative to the spinal fixation rod 208 and cannot orbit around the driver shaft 102. In the illustrated embodiment, first and second arms of the distal mating tip 190' can contact and hold lateral surfaces of the rod and can define a space between a superior surface of the rod 208 and the distal mating tip 190' to allow for distal movement of the counter torque shaft 104' when the driver shaft 102 moves distally as it tightens the implant. Because the counter torque shaft 104' can be independently rotated relative to the second gear 120b and the second connector member 122b, a user can also rotate the counter torque shaft 104' about its longitudinal axis as needed so as to align the distal mating tip 190' with the spinal fixation rod 208. With the distal mating tip 190' engaged around the fixation rod 208, the handle 106 can be manually rotated or a user can activate a power source to begin rotating the handle 106 so as to overcome the friction between the handle 106 and the first connector member 122a and begin driving the implant 200 within the receiver head 202. In the illustrated embodiment, the handle 106 is rotated in a clockwise direction and this can cause the first and second gears 120a, 120b to rotate in a clockwise and counter clockwise direction, respectively. Rotation of the second gear 120b and the constrained ends of the shafts 102, 104' will cause the second gear 120b and the counter torque shaft 104' to try to orbit around the first gear 120a in the opposite direction as the handle 106 is rotated. Because the distal mating tips 190, 190' of both the driver shaft 102 and the counter torque shaft 104' are axially constrained relative to the implants 200, 208, the first and second connector members 122a, 122b are also in a constrained axial and rotational position such that the second connector member 122b cannot orbit around the first connector member. This prevents the counter torque shaft 104' from orbiting in the opposite direction as the rotation R1 of the handle 106 and the anatomical structure/implant onto which the counter torque shaft 104' is engaged will apply a constraining force to the counter torque shaft 104'. As the implant 200 is driven into the receiver head 202, the rotational force/torque applied to the handle 106 is increased to counteract the resistance from the implant 200 and the counter torque force applied by the counter torque shaft 104' increases.

While the method steps described above involve rotating the handle 106 of the driver in a first (e.g., clockwise) direction to drive an implant 200 distally within a receiver head 202, the handle 106 can be rotated in the opposite direction (e.g., counter clockwise) to move the implant 200 proximally within the receiver head 202 to loosen the implant 200 and/or to release the implant 200 from the receiver head 202. Additionally, any of the method steps above can be performed with a device having any combination of features previously described.

The drivers herein can be assembled and/or disassembled as desired (i.e., one or more of the components of the driver can be manually removed by a user). For example, in drivers that include one or more shafts with adjustable lengths, a user can advance or retract the shaft to increase or decrease the length of the shaft to accommodate a particular surgical site. Additionally or alternatively, a user can release a distal mating tip from one or both of the shafts and insert a new distal mating tip selected to mate with a particular type of implant. Where the distal mating tip is integrally formed on or otherwise cannot be selectively released from the driver shaft, the entire driver shaft can be removed from the handle and replaced with a second driver shaft having a desired type of distal mating tip and/or the entire counter torque shaft can be removed from the second connector member and replaced with a second counter torque shaft having a desired type of distal mating tip. More specifically, this can include removing the housing from the driver, applying a force to pull apart the first and second connector members and removing one or more shafts by pulling the shaft out of the handle or the first connector member.

Figure 11:
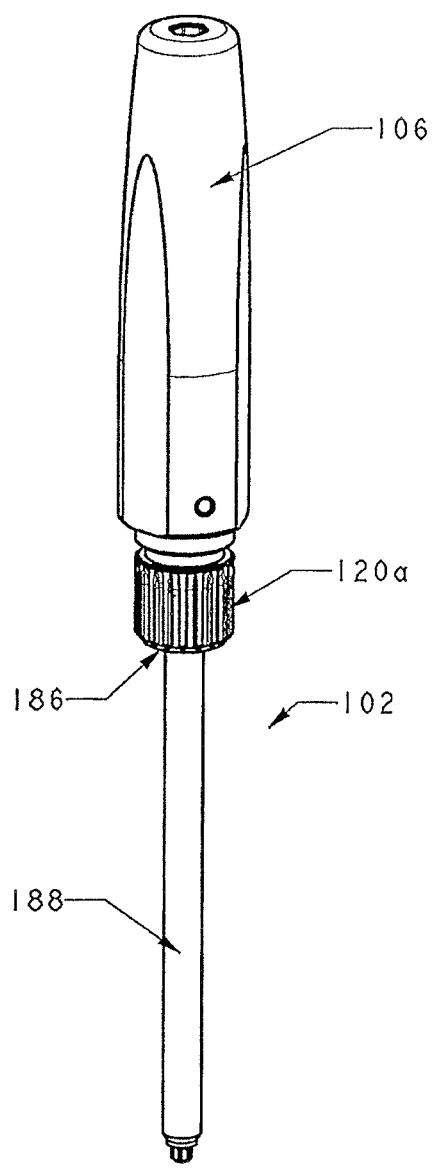
FIG. 11 is a perspective view of the driver of FIG. 1 with the counter torque shaft and the connector member removed from the device.

The ability to selectively assemble and disassemble components of the device as desired can improve the device's versatility and ability to accommodate various surgical sites. As shown in FIG. 11, the first connector member, the second connector member and the counter torque shaft can be released from the driver and the driver can be used alone without the counter torque shaft to drive an implant.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

The devices and methods disclosed herein can be used in minimally-invasive surgery and/or open surgery. While the devices and methods disclosed herein are generally described in the context of driving a first implant relative to a second implant, it will be appreciated that the methods and devices disclosed herein can be used with any human or animal bone, implant, non-living object, and so forth.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A surgical method, comprising:
  engaging an implant with a driver shaft of an instrument, the instrument having a handle at its proximal end, the implant being positioned within a receiver head of a bone anchor implanted in a patient's spine, the receiver head having a spinal rod inserted therethrough;
  positioning a countertorque shaft of the instrument in contact with the spinal rod at a location offset from the receiver head; and
  rotating the handle in a first direction to drive the implant distally within the receiver head to lock the spinal rod within the bone anchor, the countertorque shaft bearing against the spinal rod during said rotation to apply a counter torque.

2. The method of claim 1, wherein rotating the handle in the first direction comprises moving a first drive mechanism coupled to the driver shaft in a first direction, and moving a second drive mechanism coupled to the countertorque shaft in a second, opposite direction.

3. The method of claim 1, wherein rotating the handle comprises manually rotating the handle.

4. The method of claim 1, further comprising using a power source to rotate the handle in the first direction.

5. The method of claim 1, wherein a longitudinal axis of the handle is parallel to a central longitudinal axis of the implant.

6. The method of claim 1, further comprising aligning a longitudinal axis of the handle with a longitudinal axis of the implant during rotation of the instrument.

7. The method of claim 1, further comprising releasing the countertorque shaft from the instrument, engaging the implant with the driver shaft, and rotating the driver shaft without applying a counter torque via the countertorque shaft.

8. The method of claim 1, wherein positioning the countertorque shaft in contact with the spinal rod comprises disposing a recess located at a distal end of the countertorque shaft around a portion of the spinal rod.

9. A surgical method, comprising:
  driving a bone anchor into a surgical site on a patient, the bone anchor having a receiver head coupled thereto;
  inserting a fixation rod through the receiver head;
  positioning an implant within the receiver head;
  inserting a driver shaft of an instrument into the surgical site such that a distal end of the driver shaft is coupled to the implant, the instrument having a handle at its proximal end;
  positioning a countertorque shaft of the instrument at a location offset from the receiver head such that a distal tip of the countertorque shaft engages the fixation rod to constrain the countertorque shaft from orbiting the driver shaft; and
  rotating the driver shaft to drive the implant distally within the receiver head to lock the fixation rod within the receiver head, the countertorque shaft applying a countertorque force during said rotation of the driver shaft.

10. The method of claim 9, wherein rotating the driver shaft comprises rotating the handle in a first direction.

11. The method of claim 10, wherein rotating the handle in a first direction causes a first gear of the instrument to move in the first direction and a second gear of the instrument to move in a second, opposite direction.

12. The method of claim 9, wherein the surgical site comprises a vertebra of the patient.

13. The method of claim 9, wherein the driver shaft and the countertorque shaft are inserted through a single incision formed in the patient.

14. The method of claim 9, further comprising:
   driving a second bone anchor having a second receiver head into a surgical site on the patient, the surgical site being located on an adjacent level of the spine,
   inserting the fixation rod through the second receiver head,
   positioning a second implant within the second receiver head,
   engaging the driver shaft with the second implant, and
   rotating the driver shaft to drive the second implant distally within the second receiver head to lock the fixation rod within the second receiver head.

15. The method of claim 9, further comprising activating a torque limiter coupled to the handle to limit a torque applied by the driver shaft to the implant.

16. The method of claim 9, wherein the implant comprises a set screw.

17. The method of claim 9, further comprising releasing the countertorque shaft from the instrument, engaging the implant with the driver shaft, and rotating the driver shaft without applying a counter torque via the countertorque shaft.

\* \* \* \* \*